United States Patent
Gronfier et al.

(10) Patent No.: US 11,565,077 B2
(45) Date of Patent: Jan. 31, 2023

(54) WEARABLE HEALTH AND LIFESTYLE DEVICE

(71) Applicants: Institut National de la Sante et de la Recherche Medicale (Inserm), Paris (FR); UNIVERSITE CLAUDE BERNARD LYON 1, Villeurbanne (FR); ECOLE NATIONALE DES TRAVAUX PUBLICS DE L'ETAT (ENTPE), Vaulx en Velin (FR)

(72) Inventors: Claude Gronfier, Lyons (FR); Dominique Dumortier, Venissieux (FR)

(73) Assignees: Institut National de la Sante et de la Recherche Medicale (Inserm), Paris (FR); UNIVERSITE CLAUDE BERNARD LYON 1, Villeurbanne (FR); ECOLE NATIONALE DES TRAVAUX PUBLICS DE L'ETAT (ENTDE), Vaulx en Velin (FR)

( * ) Notice: Subject to any disclaimer, the term of this patent is extended or adjusted under 35 U.S.C. 154(b) by 144 days.

(21) Appl. No.: 15/756,808

(22) PCT Filed: Sep. 2, 2016

(86) PCT No.: PCT/EP2016/070753
§ 371 (c)(1),
(2) Date: Mar. 1, 2018

(87) PCT Pub. No.: WO2017/037250
PCT Pub. Date: Mar. 9, 2017

(65) Prior Publication Data
US 2018/0264224 A1     Sep. 20, 2018

(30) Foreign Application Priority Data
Sep. 2, 2015 (EP) .................................. 15306351

(51) Int. Cl.
*A61M 21/02*     (2006.01)
*A61B 5/00*      (2006.01)
(Continued)

(52) U.S. Cl.
CPC ............... *A61M 21/02* (2013.01); *A61B 5/01* (2013.01); *A61B 5/1112* (2013.01);
(Continued)

(58) Field of Classification Search
CPC ........ A61B 5/01; A61B 5/1112; A61B 5/1118
See application file for complete search history.

(56) References Cited

U.S. PATENT DOCUMENTS 5,883,740 A * 3/1999 Chubb ..................... A41D 1/00
                                                  359/350
9,146,304 B2 * 9/2015 Land ....................... G01S 7/497
(Continued)

FOREIGN PATENT DOCUMENTS

WO    WO 2008/157622 A1    12/2008

OTHER PUBLICATIONS

International Search Report dated Nov. 9, 2016 in PCT/EP2016/070753 filed Sep. 2, 2016.

*Primary Examiner* — Lynsey C Eiseman
*Assistant Examiner* — Amanda L Steinberg
(74) *Attorney, Agent, or Firm* — Oblon, McClelland, Maier & Neustadt, L.L.P.

(57) ABSTRACT

A wearable health and lifestyle device including at least a measurement module configured to be worn by a user in at least a first wearing position, the measurement module comprising a 3-axis accelerometer unit configured to provide acceleration data and inclination data, a temperature measurement unit configured to provide temperature data, a light radiation measurement unit configured to provide light radiation data, said light radiation measurement unit com-
(Continued)

Figure 1:
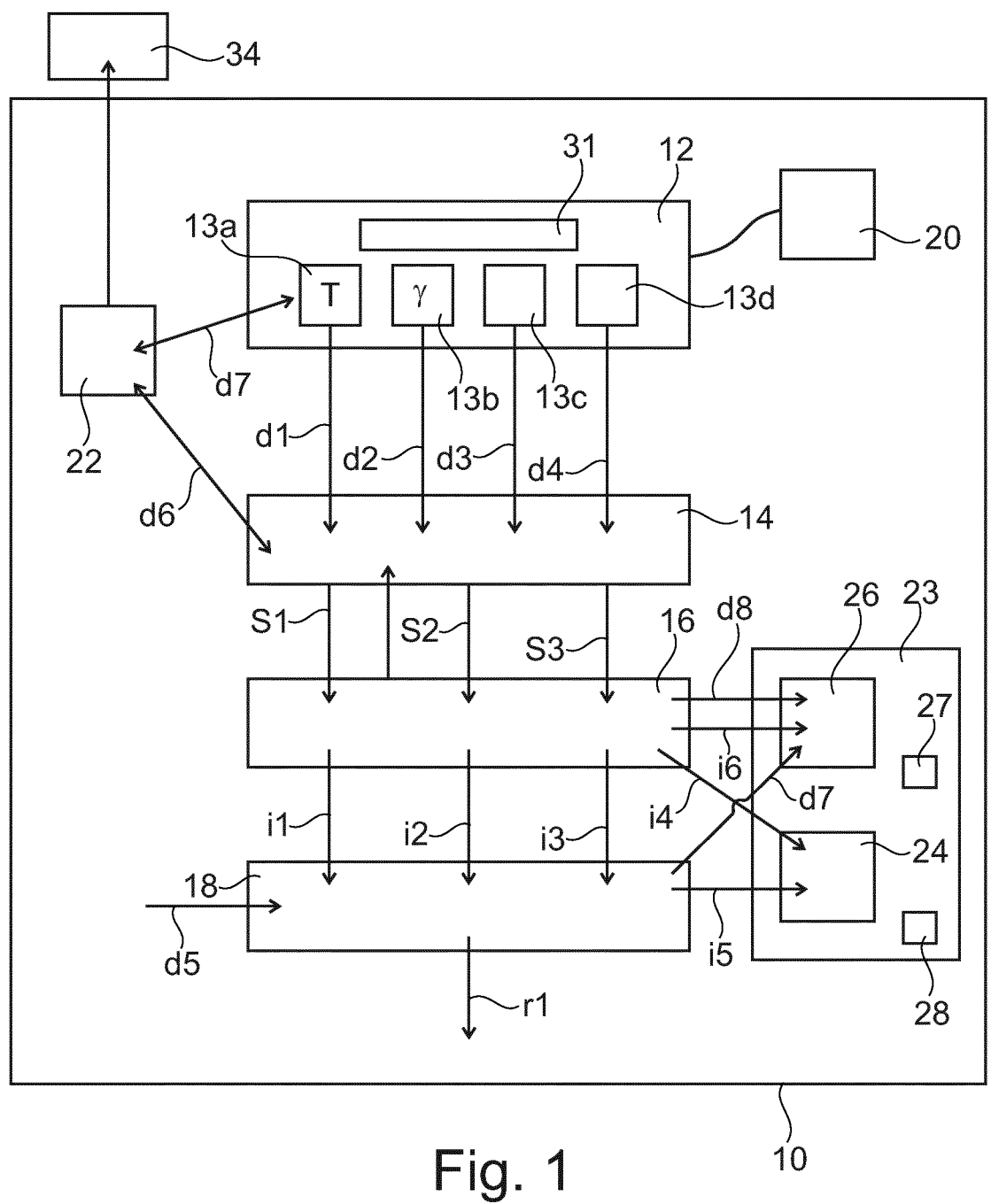

prising at least one multi-spectral sensor configured to measure wavelength bands over the range 290 nm to 1150 nm, a storage module configured to receive and store said acceleration data, said inclination data, said temperature data and said light radiation data, and an analysis module configured to analyze a data set comprising acceleration data, inclination data, temperature data and light radiation data.

18 Claims, 2 Drawing Sheets

(51) Int. Cl.
  *A61B 5/01*    (2006.01)
  *A61B 5/11*    (2006.01)
  *A61N 5/06*    (2006.01)
  *H04W 4/02*   (2018.01)
  *A61M 21/00*   (2006.01)

(52) U.S. Cl.
  CPC .......... *A61B 5/1118* (2013.01); *A61B 5/4809* (2013.01); *A61B 5/4836* (2013.01); *A61B 5/4857* (2013.01); *A61B 5/681* (2013.01); *A61B 5/6803* (2013.01); *A61B 5/6898* (2013.01); *A61N 5/0618* (2013.01); *A61B 2560/0242* (2013.01); *A61B 2562/0219* (2013.01); *A61M 2021/0044* (2013.01); *A61M 2021/0066* (2013.01); *A61M 2205/332* (2013.01); *A61M 2205/3303* (2013.01); *A61M 2205/3306* (2013.01); *A61M 2205/3584* (2013.01); *A61M 2205/3592* (2013.01); *A61M 2205/505* (2013.01); *A61M 2205/52* (2013.01); *A61M 2205/582* (2013.01); *A61M 2209/088* (2013.01); *A61M 2230/50* (2013.01); *A61M 2230/63* (2013.01); *A61N 2005/0628* (2013.01); *A61N 2005/0645* (2013.01); *H04W 4/025* (2013.01)

(56) References Cited

U.S. PATENT DOCUMENTS

| | | | |
|---|---|---|---|
| 2009/0012433 A1 | 1/2009 | Fernstrom et al. | |
| 2009/0281604 A1* | 11/2009 | De Boer | G09G 3/3413 345/83 |
| 2011/0248171 A1* | 10/2011 | Rueger | G01S 11/12 250/340 |
| 2012/0296400 A1* | 11/2012 | Bierman | A61M 21/00 607/88 |
| 2013/0267794 A1 | 10/2013 | Fernstrom et al. | |
| 2014/0267299 A1* | 9/2014 | Couse | G06T 11/206 345/440.2 |
| 2014/0275850 A1 | 9/2014 | Venkatraman et al. | |
| 2014/0318699 A1 | 10/2014 | Longinotti-Buitoni et al. | |
| 2015/0102208 A1* | 4/2015 | Appelboom | G01J 1/4204 250/208.2 |
| 2015/0143601 A1 | 5/2015 | Longinotti-Buitoni et al. | |
| 2015/0230735 A1 | 8/2015 | Venkatraman et al. | |
| 2016/0066844 A1 | 3/2016 | Venkatraman et al. | |
| 2016/0123802 A1* | 5/2016 | Likovich | G01J 1/0271 356/221 |
| 2016/0129280 A1* | 5/2016 | Douglas | A61M 21/00 607/88 |
| 2016/0341436 A1* | 11/2016 | Parker | A61B 5/318 |
| 2017/0249824 A1* | 8/2017 | Kaplan | A61B 5/18 |

* cited by examiner

WEARABLE HEALTH AND LIFESTYLE DEVICE

The present invention deals with a wearable healthcare and lifestyle device acting as a personal assistant regarding the exposure to light, physical activity, and sleep patterns of a user, and as a personal advisor in relationship with his lifestyle and noticeably his sleep and circadian rhythms.

STATE OF THE ART

Recent scientific research in the healthcare domain has highlighted the presence of non-classical photoreceptors on the surface of human eye retina (called ipRGCs, for intrinsically photosensitive retinal ganglion cells), which are not involved in visual information like rods and cones, but in non-visual functions of the brain. Those cells have been shown to be maximally sensitive to 480 nm light, and to inform a number of brain structures that are not involved in vision, contrary to rods and cones. This discovery has confirmed the influence of the environmental light, particularly daylight, on biological rhythms and on health and well-being of every single human being. It has also provided a scientific basis to understand and optimize the efficiency of the phototherapy (or light therapy) approaches as ways to treat pathologies such as seasonal affective disorder, non-seasonal depression, sleep disorders, as well as linking light exposure with activation of cerebral structures involved in regulating circadian rhythms, memory, mood, alertness and sleep.

Since this discovery, lighting devices have been developed to provide a specific light spectrum which is supposed to improve the feeling of comfort of the user who is exposed to it. Usually, these devices provide a light spectrum which emphasizes the blue component, in a wavelength spectrum ranging between 460 nm and 500 nm. Some of them provide different lighting scenarii, by tuning the blue component intensity according to the time of the day, which is supposed to provide an improved feeling of comfort to the user. However, the clinical efficiency of such lighting devices has not always been scientifically demonstrated.

Although it is known that proper daily light exposure is necessary to synchronize the human body clock and promote a good sleep, how environmental natural and artificial light precisely affects biological rhythms and non-visual functions is still unknown as it has never been assessed properly.

While some components of the light spectrum may be beneficial to humans, others may be harmful, i.e. phototoxic, particularly the ultraviolet, below 400 nm, and the short wavelengths of the visible, from 400 nm to 460 nm. Excessive exposure to UV leads to photokeratitis, photoconjectivitis and cataracts. Excessive exposure to light below 460 nm has been associated to Age related Macular Degeneration (AMD) and is called the "blue light hazard". Photochemical damage is related to a short-time intense exposure or a prolonged exposure to lower levels. Guidelines from the International Commission on Non Ionizing Radiation Protection (ICNIRP) provide exposure limits. Additionally, although light, and in particular non-visual blue light around 480 nm, is necessary as described above, exposure to light at inappropriate times has been shown to induce disorders, including sleep disorders (for example light at night, or LED use before bedtime).

Lifestyle evaluation devices have been developed, which measure different parameters related to the user, for example acceleration and visual light exposure, and to his environment, for example surrounding light and/or environment temperature. However, these devices measure only visual, i.e. photopic, without measuring "non-visual blue-light" (ipRGC) exposure, or they do not measure UV light exposure, or they do not measure exposure to "phototoxic" blue light, or they do not measure infrared to differentiate between natural and artificial light, or they do not measure temperature to correct light measures and improve sleep assessment, or they measure light exposure at the wrist and not at the eye, or they don't assess sleep (through the activity cycle). Thus, the information that might be analysed from said measurement is generally much less meaningful, and may even be erroneous.

For instance, the Actiwatch Spectrum Plus® device marketed by Philips presents the shape of a wrist watch. It comprises a storage module, an actimeter consisting in an accelerometer which measures the level of activity of the user, and a set of four photodiodes configured to measure the light photopic illuminance and its spectral irradiance over three wavelength ranges centred around 655 nm, 500 nm and 460 nm, corresponding to red, green and blue colours respectively. The Actiwatch Spectrum Plus® can measure and store the user acceleration and light intensities every fifteen minutes for nine days. It is also provided with an USB plug to transfer all the stored data to a personal computer. However, since this device is worn on the wrist, it does not measure the light received by the eye, and most of all, it may be covered by clothes worn by the user which is a cause of measurement error. It is therefore not well suited for estimating light received at the eye level.

The LuxBlick® device, developed by the Center of Organizational and Occupational Sciences, Environmental Ergonomics of ETH Zurich, comprises sensors which are attached on an eyeglass frame and which measure, using appropriate filters, the photopic and ipRGC illuminance reaching the eyes of a user. The two sensors are connected using wires to a storage module which is placed into a pocket of the user. It does not provide any information concerning the user activity and sleep.

US 2012/0296400 discloses a device named Daisymeter®, which has been developed by the Lighting Research Center, Rensselaer Polytechnic Institute of Troy, USA. This device is attached on an eyeglass frame of a user, and comprises two photodiodes which measure the intensity of the light received by the eyes of the user, as well as an accelerometer at the head level, which provides information about the user activity while wearing the device. It does not provide any information concerning the user activity and sleep.

Overall, none of the devices provides simultaneous information regarding the user sleep and wake state, and how the user has been exposed to non-visual light at the eye level (UV, phototoxic, IR, and melanopic light). For instance, in the case of a user wearing a device with an accelerometer and a light sensor on the wrist, the acceleration data will be possibly precise enough to assess sleep and wake states, but the light exposure will be meaningless. Indeed, not only light will be measured far from the eye, but the device will be occasionally covered by the user sleeves, for instance of a sweater or a coat. On the other hand, in the case of a user wearing a device with an accelerometer and a light sensor at the head level, the light data will be possibly precise enough to assess visual light, but not enough for non-visual light, and the accelerometer data recorded at the head level will not practically allow the device to assess sleep and wake states.

Also, existing devices on the market may provide a very imprecise estimate of sleep and wake states. The newest scientific literature shows that knowledge of night time temperature, in addition to accelerometry, enhances sleep and wake estimates. Additionally, knowledge of temperature during daytime improves the accuracy of the photosensors used to measure light exposure, as well as serves as an indicator of indoor or outdoor conditions.

Therefore, there is a need for a device which provides improved and accurate information on light type exposure (UV, light below and above 460 nm, infrared), physical activity, quality of sleep and wake, and lifestyle of a user.

SUMMARY OF THE INVENTION

The invention aims at solving these problems and succeeds in it by providing a wearable health and lifestyle device comprising at least a measurement module configured to be worn by a user in at least a first wearing position, the measurement module comprising a 3-axis accelerometer unit configured to provide acceleration data and inclination data, a temperature measurement unit configured to provide temperature data, and a light radiation measurement unit configured to provide light radiation data, said light radiation measurement unit comprising at least one multi-spectral sensor configured to measure wavelength bands over the range 290 nm to 1150 nm, said device further comprising a storage module configured to receive and store said acceleration data, said inclination data, said temperature data and said light radiation data, and an analysis module configured to analyse a data set comprising acceleration data, inclination data, temperature data and light radiation data acquired all along a period of time greater than 24 hours and stored in the storage module, so as to provide information regarding a user physical activity, and a wake/sleep state, the temperature measurement unit being configured to measure the user body temperature in the first wearing position.

Advantageously, thanks to the device according to the invention, whether the user is asleep or awake may be determined from the data set comprising acquired acceleration data, inclination data and body temperature data in the first wearing position. For example, when at night the user moves the device from the second position to the first position, the analysis module detects that the measured temperature increases from room temperature to body temperature and provides as information that the night period has begun. Furthermore, during the night, the body temperature variation is measured. In a concurrent way, the acceleration and inclination are recorded. For instance, it is well known that the temperature of the human body decreases during sleep, and that the activity is slowed down. Therefore the analysis of sets of body temperature, acceleration data and inclination data inform about whether the user is asleep during the night time period, and if so about his sleep quality. In addition, in the second wearing position, data regarding the ultraviolet (UV A and UV B), the visible and the near infrared range (NIR) of outdoor daylight may be collected thanks to the multi-spectral sensor. Provided with the light radiation data acquired from the at least one multi-spectral sensor, the analysis module may further provide information to the user to assess whether he/she has been properly or improperly exposed to light, in terms of intensity, spectrum and timing, or in terms of indoor and outdoor light.

By providing a detailed analysis of a whole set of acceleration data, said inclination data, temperature data and light radiation data, the device according to the invention provides improved information with regard to the prior art to assess the user lifestyle, and allows to provide health-related recommendations, and to control the environment (lighting, . . . ).

A device according to the invention may also comprise one or more of the following optional features:
- the storage module is further configured to receive and store geographic coordinates data, the analysis module being further configured to analyse a set of geographic coordinates data acquired all along the period of time in order to compute sunrise and sunset hours in view of providing information regarding user daylight exposure and bedtime;
- the measurement module comprises a Global Positioning System (GPS) unit configured to acquire the geographic coordinates data;
- the device comprises a communication unit configured to receive the geographic coordinates data sent from an apparatus, the apparatus comprising a GPS unit configured to acquire and/or store the geographic coordinates data;
- the apparatus is chosen among a smartphone or a watch;
- the measurement module is further configured to be worn by the user in a second wearing position different from the first wearing position;
- the first wearing position is on the wrist and the second wearing position is on an eyeglass frame;
- in the first wearing position, the temperature measurement unit measures the skin temperature and in the second wearing position, the temperature measurement unit measures the environment temperature;
- the analysis module is configured to analyse from the data set at least one among temperature data, inclination data and light radiation data in order to compute user bedtime;
- the analysis module is configured to analyse from said data set at least one among temperature data, acceleration data, inclination data and light radiation data, in order to provide information on the user sleep/wake state;
- the analysis module is further configured to analyse from the data set, at least temperature data and light radiation data in order to provide a set of temperature corrected light radiation data;
- the analysis module is configured to analyse from the data set at least light radiation data in order to provide information regarding the user exposure to UV, i.e. a radiation having a wavelength smaller than 400 nm, and/or to phototoxic blue light having a wavelength between 400 and 460 nm, and/or to non-visual blue light having a wavelength between 460 and 500 nm, and/or to photopic light having a wavelength of between 380 and 780 nm, and/or to IR having a wavelength above 780 nm during said period of time;
- the device comprises a wristband and/or temporary fixing means to an eyeglass frame, the wristband and fixing means being configured for the fixing of the measurement module;
- the device comprises a synthesis module configured for assessing a user lifestyle from a set of information supplied by the analysis module, preferably all along said time period, and said set of information preferably comprising information regarding the user sleep/activity history and/or its exposure history to daylight and/or to UV and/or to blue light radiation;
- the synthesis module is configured to provide recommendations for improvement of the user lifestyle, said recommendations consisting in:

defining a minimum and/or maximum dose of exposure to daylight and/or artificial light, and/or defining a minimum and/or maximum dose of exposure to a radiation having a wavelength smaller than 400 nm, and/or to phototoxic blue light having a wavelength between 400 and 460 nm, and/or to non-visual blue light having a wavelength between 460 and 500 nm, and/or to photopic light having a wavelength of between 380 and 780 nm, and/or to infrared light having a wavelength above 780 nm, in particular defining a minimum and/or maximum dose of exposure to UV, and/or blue light below 460 nm, and/or blue light above 460 nm, and/or defining one or more spectrum(s) of artificial light suitable to the user at a given time of the day, and/or controlling at least one home apparatus, in particular turning a light on or off, or dimming or brightening a light, or modifying the spectrum of a light, or opening or closing blinds, and/or defining a schedule for sleeping and/or awakening and/or exposing the user to daylight and/or said artificial light, and/or controlling said apparatus;

the device comprises a user interface module configured to provide and/or acquire information to/from the user;

the user interface module comprises at least one unit chosen among a display only or touchscreen unit, an audible signal unit, a vibrating unit and a push-button unit;

the device comprises a communication unit configured to provide communication between at least two modules chosen among the measurement module, the storage module, the analysis module, if appropriate the synthesis module, if appropriate the user interface module, at least one module consisting of at least a home apparatus and a mobile module consisting in a mobile phone;

the time period is preferably greater than 1 week, preferably even greater than 1 month;

the information regarding the sleep state and/or the information regarding the indoor or outdoor location and/or the information regarding the user body provided by the analysis module may be sent and stored in the storage module.

When the user wears the device in the second wearing position during daytime and in the first wearing position during night-time, the steep variation in the measurement of the temperature between the first and second wearing positions provides further information on the daytime/night-time transition, since the environment temperature is generally lower than the body temperature. The analysis module may then provide a supplemental confirmation that the user is asleep, or is about to go to bed. Acceleration data may help determining whether the user is awake or asleep.

Figure 2:
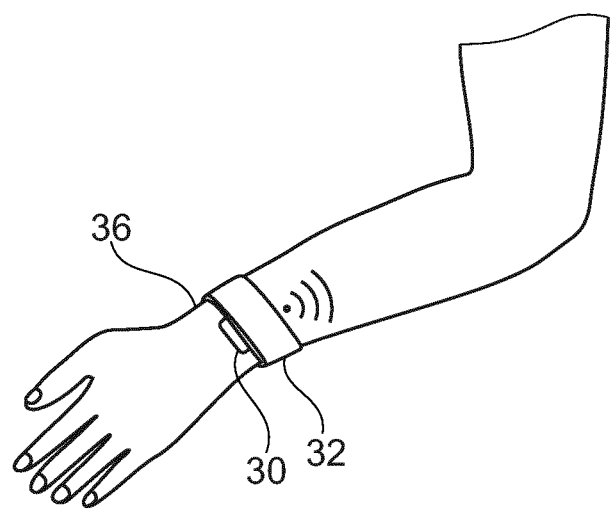
Figure 3:

The invention may be better understood from the reading of the detailed description that follows, with reference to exemplary and non-limiting embodiments thereof, and by the examination of the appended drawing, in which:

FIG. 1 shows in a synoptic diagram the modules of a device according to an embodiment of the invention, and FIGS. 2 and 3 illustrate first and second wearing positions respectively of the device according to the invention.

In the appended drawing, the actual proportions of the elements constituting the lifestyle estimation device are not always respected, in a concern for clarity of the drawing.

As illustrated on FIG. 1, a device 10 according to the invention comprises a measurement module 12 which comprises measurement units 13 *a-d* configured to acquire data during a period of time and to provide said data to a storage module 14 configured to receive and store said data d1-d4. The device also comprises an analysis module 16, which is configured to communicate with the storage module. The analysis module is configured to receive said data from the storage module and to analyse said data such as to provide as an output several kinds of information regarding the user sleep state as it will be more apparent in the following.

The device can also comprise a synthesis module 18 which is configured to receive as an input and to synthesize the information provided by the analysis module, in order to assess as an output the lifestyle diagnostic of the user of the device.

It may also comprise a battery 20 which supplies power to the modules and units of the device, a communication unit 22, and a user interface module 23, comprising at least one unit chosen among a display only or touchscreen unit 24, an audible signal unit 26, a vibrating unit 27 and/or a pushbutton unit 28. Preferably, these constituents are installed in a casing 30.

Measurement Module

The measurement module comprises at least two measurement units: a 3-axis accelerometer unit 13*b* configured to measure acceleration data γ and inclination data α and a temperature measurement unit 13*a* configured to measure temperature data T. It also preferably comprises a clock and is configured to associate time measured by the clock to any measurement performed by at least one of the measurement units.

Preferably the inclination data comprise angular positions relative to horizontal and vertical directions.

In particular, the 3-axis accelerometer unit provides information relative to the acceleration and inclination relative to horizontal and vertical directions. For instance, in case the 3-axis accelerometer unit is worn in the second wearing position, for instance on the head of the user, the measurement module is preferably adapted to measure the inclination and the acceleration of said head.

Preferably, the acceleration measurement unit is adapted to measure acceleration within ±3G. In particular, when the measured acceleration is less than 0.1 m·s$^{-2}$, it is considered that the portion which wears the acceleration measurement unit is almost still.

Preferably, the temperature measurement unit 13*a* comprises a temperature probe measuring temperature by contact or remotely. For example, the temperature probe can be a thermo-resistance or a remote infrared or laser thermometer. Preferably it is adapted to measure temperature in the range −20° C. to +50° C.

In a preferred embodiment, the measurement module comprises a light radiation measurement unit 13*d*. Preferably, the light radiation measurement unit comprises a light probe, preferably at least one multi-spectral sensor adapted to measure wavelengths ranging from 290 nm (ultraviolet) to 1150 nm (infrared) over at least eight spectral bands, including at least one in the UV range, and at least one in the infrared range.

Advantageously, a spectral sensor provides a much more detailed measurement of the light spectrum than RGB photosensors. This allows to determine how the light affects the photopic sensitivity of the user, i.e. the sensitivity of his/her visual system, as well as the melanopic sensitivity of the user, i.e. the non-visual sensitivity, including sensitivity of his/her circadian system. It also allows to determine more precisely to what light source the user is exposed. Provided with the light radiation data acquired from the at least one multi-spectral sensor, the analysis module may provide information to the user and/or to the synthesis module to assess whether he/she has been properly or improperly exposed to light, in terms of intensity, spectrum and timing, or in terms of indoor and outdoor light. The synthesis module may then provide as an output, recommendations consisting in performing precise actions, such as decrease or increase light exposure for example. More specifically, the analysis module may analyse from the light radiation data the amount of light in the melanopic range of the light spectrum (460-500 nm), resulting in an assessment of the amount of "non-visual" light received by the user. It may analyse the amount of light in the blue range of the light spectrum (400-460 nm), which may result in an assessment of the amount of phototoxic light received by the user. It may even analyse the amount of light in the UV (A and B) range of the light spectrum (<400 nm), which may result in an assessment of the amount of phototoxic and skin-toxic light received by the user.

The measurement module is adapted to measure acceleration data and/or inclination data and/or temperature data and/or light radiation data all along a time period which is greater than 24 hours, preferably greater than a week, even preferably greater than two weeks.

The measurement module may also comprise a GPS unit 13c configured for acquiring geographic coordinates. The GPS unit may send a set of geographic coordinates for being stored to the storage module.

The measurement module is preferably configured so that the sensitivity range and the sampling rate of each measurement unit may be adjusted independently. As an example, the time step between two immediately successive measurements is as low as 0.01 s (100 Hz) on the accelerometer unit and as high as 60 seconds (0.02 Hz) on the temperature and on the light radiation units.

The measurements are then processed in order to define a set of data which is stored in the storage module.

Storage Module

The storage module 14 is configured to receive the data measured by the measurement module and to store said data. It may also be configured to store data output by the analysis module.

In particular, the amount of storage memory of the storage module is adapted such as to store data provided by each of the measurement units all along said period of time. For instance, the storage memory is adapted to store acceleration data for at least four weeks.

The storage module may be configured to replace the oldest stored data by new received data when the storage module memory is full. In this way, the storage module has the capacity for all the data received during said period of time.

The storage module may be placed in different locations with respect to the measurement module. In a first variant, the storage module is integrated to the measurement module. The connection between the storage module and any of the measurement units is then preferably wired. In a second variant, the storage module is located remotely from the measurement module. Preferably, both the storage module and the measurement module comprise remote wireless connection, such as WiFi, Bluetooth, or NFC configured for the measurement module to provide data to the storage module. As an example of the second variant, the storage module can be at least part of the memory of a smartphone, or at least part of a hard disk drive of a Personal Computer or of a NAS, or of a centralized server.

In an embodiment, the storage module may also be configured to store information provided by the analysis module and/or by the synthesis module.

Analysis Module

The analysis module 16 is configured to receive a set of data s1-s3 from the storage module and to analyse said data, and from said analysis, to provide an information i1 about the user sleep state.

The analysis module may be integrated in the measurement module. Alternately, it may be part of a remote computer.

The information regarding the sleep state of the user provided as an output by the analysis module may be sent to the storage module 14 for being stored.

In another embodiment, the analysis module improves the quality of the measured data.

It is known that environmental temperature varies according to time, season and location (in the range from −20° C. to +50° C.) and this is known to affect accuracy and precision of the light radiation measurements. Therefore, the analysis module may be configured to correct among a data set, light radiation data with temperature data, preferably measured over the same period of time. This temperature correction may be applied on a set of light radiation data based on laboratory calibrations.

The analysis module may be configured to analyse the differences of the temperature-corrected light radiation data set in order to provide an information i2, about whether the user wearing the measurement module is indoor or outdoor. First, the spectra of natural light and artificial light differ. Second, the spectra of natural light measured indoor and outdoor differ. Since ultraviolet is filtered out by windows, the UV component of the light spectrum outdoor is more pronounced than indoor, whereas the IR component prevails. As another example, in summer, the presence of UV wavelength in the light radiation data is usually sufficient to infer that the user is outdoor. In winter, however, under cloudy conditions, reduced amounts of UVs and lower illuminance levels are found outdoor, and only temperature data might allow to differentiate between indoor and outdoor environments.

The analysis module may also be configured to analyse among a data set, the temperature corrected light radiation data, to determine throughout said set, the amount of erythemal irradiance in the range from 290 to 350 nm, the amount of phototoxic irradiance in the range from 400 to 460 nm, the amount of photopic illuminance in the range from 380 to 780 nm, the amount of melanopic illuminance (as defined in Lucas et al. *"Trends in Neurosciences"*, January 2014, Vol. 37, No. 1) and the amount of near infrared irradiance in the range from 780 to 1150 nm.

The analysis module may be configured to integrate over periods of time of more than 1 hour, or more than 1 day, or even more than 1 week, said amounts per wavelength range to assess the total exposure, i.e. dose, of the user.

In case the measurement module comprises a Global Positioning System (GPS) unit, geographic coordinates may be used to determine the user location, and the local sunrise and sunset hours. In combination with the sleep/wake cycle derived from accelerometer and temperature, this is useful to assess how an individual is adjusted to the light-dark cycle.

The analysis module may be adapted for analysing both a set of acceleration data and a set of inclination data, such as to assess posture and physical activity of the user. The analysis module may be adapted to analyse both a set of temperature data and a set of acceleration data such as to inform whether the device is worn by the user, and where, notably in the first or second wearing position. For example, data comprising almost null acceleration for more than 5 minutes could either mean that the user is asleep or that he has forgotten to wear the device. The joint analysis of temperature and light radiation data measured over the same time period may discriminate between the two situations. As an illustration, temperature data in the range of skin temperature, for instance between 32 and 35° C., jointly with null acceleration for more than 5 minutes, and light radiation indicative of darkness, will provide the information i3 that the user is asleep, wearing the device in the first wearing position, for example on the wrist.

The analysis module may be configured to analyse with an algorithm detailed in Cole ("*Automatic sleep/wake identification from wrist activity*", Cole R. J. et al., Sleep, October 1992, 15(5):461-9), among a data set, body temperature data provided by the temperature measurement unit in case the device is worn in the first wearing position, for instance on the wrist, together with acceleration data provided by the accelerometer unit. The analysis module can thus provide a more accurate definition of sleep states than the one resulting from the analysis of a single set of acceleration data. The analysis module may be further adapted to analyse among a data set, acceleration data together with inclination data, and together with temperature data, in particular for different wearing positions, noticeably including the first wearing position, using a mathematical method detailed in Ortiz-Tudela et al. ("*A New Integrated Variable Based on Thermometry, Actimetry and Body Position (TAP) to Evaluate Circadian System Status in Humans*", PLoS Comput Biol 6(11): e1000996. doi:10.1371/journal.pcbi.1000996), to assess the state, i.e. the internal time, of the circadian biological clock. The analysis module may then provide as an information both the user circadian and sleep/wake states.

Synthesis Module

The device may also comprise a synthesis module 18 configured to assess a user lifestyle over the period of time from a set of information supplied by the analysis module and/or read from the storage module.

It may be also configured to provide recommendation r1 for improving said user lifestyle.

The synthesis module may be integrated with the measurement module and/or the analysis module. Alternately, it may be part of computer.

The synthesis module may also be configured to receive data directly provided by the user d5. As an illustration, the user may provide as an input to the synthesis module an objective to be achieved, which for example may be defined as the duration to which he/she should be exposed to daylight, or the minimal amount of physical activity that he/she should perform.

As another example, the synthesis module may recommend the user to expose himself/herself to a specific light (intensity, wavelength), at a precise time of the day, for example to improve his/her sleep quality, or to reduce his/her depressive symptoms.

As another example, thanks to the accuracy of the light radiation measurement unit, the synthesis module may be configured to monitor and inform the user about his/her cumulated exposure to health-related light radiations (UV, blue light hazard).

Other Units

In particular, when the storage module and/or the analysis module and/or the synthesis module are remote from the measurement module, the device may comprise a communication unit 22 configured to transfer data d6, d7 to the storage module and/or the analysis module and/or the synthesis module.

The communication unit may also be used to communicate with one or more apparatus 34 located in the environment of the user. Thus, the invention also relates to a system comprising such apparatus and a device according to the invention. Apparatus 34 may be chosen in the group constituted by a lighting fixture, an alarm clock, a window blind, a thermostat.

Preferably, the communication unit controls one or more apparatus 34 according to the information provided by the analysis module or by the synthesis module.

In particular, the communication unit may comprise a remote wireless connection, such as WiFi, or preferably Bluetooth, or NFC, or a wired connection, for example a USB connection.

In a specific embodiment, the device may comprise a display unit 24 which is configured to receive any of the information i4, i5 provided by the analysis module and/or the synthesis module and to display said information. In an embodiment, the display unit may only be checked by the user in case the measurement module is worn in the first wearing position, for instance on the wrist.

The device may also comprise an audible signal unit 26, such as an alarm, which may be configured to vibrate and/or to produce an audible and/or a visible signal. It may be configured to receive data d7, d8, from the synthesis module or from the analysis module to inform the user that he/she is not wearing the device, that the battery of the device is low, that he/she has reached an objective, that he/she has exceeded his exposure to a specific spectrum of light, etc.

In particular, the alarm unit may be advantageously operating in case the display device cannot be checked by the user when worn in the second wearing position, in particular on an eyeglass frame. In case the measurement module is worn around the wrist, it may inform the user that this is time to go to bed or to wake up.

The casing may present the shape of a rectangular box, which greatest dimension is less than 5 cm.

Preferably, the casing is designed to be attached to a wristband 32 and/or comprises temporary fixing means 34 to an eyeglass frame. The casing may be provided with a plug 36, for example a USB plug, to transfer data toward the storage module and/or the analysis module.

Preferably, in the first wearing position, the measurement module is worn on the wrist, and in the second wearing position, it is worn on an eyeglass frame, preferably on its temple arm.

In the first wearing position, in particular on the wrist, the temperature measurement unit 13a is preferably in contact with the user skin, such as to measure the skin body temperature. The light radiation measurement unit 13d, if appropriate, is preferably disposed such that the light probe which is adapted to receive light is not facing the user body. Then, in the first wearing position, the light radiation measurement unit measures environmental light intensity, with a lower accuracy than in the second wearing position, but remains informative if for example the user turns the lights on at night (to read, to go to the toilets . . . ).

In the second wearing position, notably on an eyeglass frame, the light probe is preferably placed so that it measures the light spectrum which is effectively received in the plane of the eye.

Use of the Device

The device of the invention may be implemented as follows.

As an illustration, the user may sleep, lying in bed, with the device worn on the wrist as first wearing position. He/she may get awakened, either by the audible signal unit and/or the vibrating unit of the interface module, or with gradually increasing light intensity, for instance simulating dawn, with a home apparatus controlled by the communication unit. Time for awakening can be either pre-set before bedtime, or optimally computed by the device according to the sleep state, as determined by the analysis module described above. He/she may also awaken naturally. At wake time, the user may press the push-button unit on the interface module of the device to let the device know that he/she is awake. This improves the accuracy of the sleep analysis. At wake time, the interface module may also provide, in particular by displaying onto the display unit, results computed by the analysis module such as sleep duration and sleep efficiency. Once out of bed, the user may place the device in the second wearing position, for example on an eyeglass frame. If the user keeps the device on the first wearing position, for example on the wrist, or if he forgets to wear it at any time, he may be alerted by the device through at least one of the audible signal unit and vibrating unit of the interface module.

During daytime, the device analyses the user's exposure to light radiation to infer indoor and outdoor activities, which are related to the user lifestyle, as well as his/her exposure to specific light radiations related to his/her health. The synthesis module may recommend the user to increase or decrease his/her exposure to sunlight and/or artificial light. The device may communicate with a home apparatus, such as a lighting fixture, to increase or decrease its intensity or to modify its spectrum. For example, someone working in an office, may be recommended by the synthesis module to go outside for a determined period of time, in order to increase his/her light exposure to favour body clock adjustment, daytime vigilance, and sleep quality. In another situation, based on recommendations of the synthesis module, the communication unit may adjust the blinds to reduce glare, or turn on lighting fixtures to increase photopic illuminance and improve visual performance. In another situation, based on recommendations of the synthesis module, the communication unit may recommend the user to decrease his/her light exposure before bedtime, to avoid delay his/her biological circadian clock.

During daytime, the analysis module may compute acceleration and posture based on the accelerometer data acquired by the measurement module. According to the intensity and duration of physical activity, the synthesis module may recommend the user to change his/her posture, and to exercise, for health purposes.

In the evening, the synthesis module may inform the user about his/her optimal bedtime, and either recommend him/her to decrease physical activity, or to prepare his/her own environment, or take control of his/her environment, the device communicating with home apparatus for providing appropriate sleep conditions, in order for instance to decrease ambient temperature, light intensity or blue light content.

At bedtime, the user may place the device in the first wearing position, for instance on the wrist. He/she may press the push-button to let the device know that he/she is ready to sleep, for example after reading a book. Then, between bedtime and wake time, sets of data of light radiation, inclination, acceleration, and temperature may be analysed by the analysis module to assess the time at which the user falls asleep (sleep onset), wakes up, goes back to sleep, turns the lights on and off, and gets out of bed.

The device according to the invention may advantageously be implemented in health research programs regarding the influence of light (flux, duration, exposure) on the alertness and stress, of single people or on groups of people, for example depending on their daily work, age, etc.

It may be implemented in research programs investigating the influence of light on sleep and circadian disorders, seasonal or non-seasonal depression, metabolism disorders, memory troubles, physical activity disorders, and also for assessing photic strategies in the treatment of troubles of sleep circadian rhythm, and sleep, for example in people having neurodegenerative pathologies or affective disorders.

It may be implemented as a diagnostic tool or to assess a patient lifestyle by physicians, in particular by general practitioners or specialist physicians, in order to propose recommendations for improving said lifestyle, or for reducing symptoms, such as improving sleep in shift workers or adolescents, improving sleep hygiene in the general population, increasing physical activity, or preventing premature aging of the eye.

The device may be implemented for the monitoring of said patients in the course of light therapy treatments. For instance, it may be implemented for assessing whether adolescents, shift workers, patients have followed the recommendations made by the physician, to treat their circadian sleep disorder, or SAD, or insomnia. In this case, the device would be used as a tool for monitoring therapy compliance.

The device may be implemented for clinical applications wherein light, and in particular specific wavelengths components of the light spectrum, have an impact on health. For instance, it may be implemented in the domain of dermatology, when patients are suffering from cancer or when they are given photosensitizing medications, to monitor their exposure to light, and in particular to UV. It may be implemented in the domain of diabetology or of obesity, to monitor sleep patterns, as poor sleep has been shown to be associated with those diseases. In the field of ophthalmology, the device may be used to monitor light exposure in patients suffering from age-related macular degeneration or other eye diseases.

The device may be implemented for the control of systems in buildings or any other built environments as a way to satisfy health and comfort related requirements of users at the individual level. For instance, building occupants would wear the device so that it controls blinds, lights, heaters, coolers located in their corner, based on their activity, their biological clock, their history of light exposure, their preferences . . . .

Of course, the present invention is not limited to the embodiments described and represented, these being provided as illustrative and non-limiting examples.

The invention claimed is:

1. A wearable health and lifestyle device comprising:
at least a measurement circuit configured to be worn by a user in at least a first wearing position, the measurement circuit including a 3-axis accelerometer configured to provide acceleration data and inclination data;
a temperature measurement sensor configured to provide temperature data and to measure a user body temperature in the first wearing position;
a light radiation measurement sensor configured to provide light radiation data, said light radiation measurement sensor including at least one multi-spectral sensor configured to measure wavelength bands over a range 290 nm to 1150 nm, the multi-spectral sensor being configured to measure light radiation over at least one UV wavelength band being a first range ranging between 290 nm and 400 nm and at least one phototoxic blue light wavelength band being a second range ranging between 400 nm and 460 nm and at least one non-visual blue light band being a third range ranging between 460 nm and 500 nm;

storage circuitry configured to receive and store said acceleration data, said inclination data, said temperature data, and said light radiation data; and analysis circuitry configured to analyze a data set including at least a portion of the acceleration data, inclination data, temperature data and light radiation data acquired all along a period of time greater than twenty-four hours and stored in the storage circuitry, provide information regarding a user physical activity and a wake/sleep state, and define the first, second and third ranges such that the measuring of light radiation over each of said first, second and third wavelength bands is distinct from the measuring of light radiation over every other of said first, second and third wavelength bands, wherein the analysis circuitry is configured to analyze from the data set in order to provide:

first information regarding user exposure, during the period of time, to the first range, second information regarding user exposure, during the period of time, to phototoxic blue light having the second range, and third information regarding user exposure, during the period of time, to non-visual blue light having the third range, wherein the analysis circuitry is further configured to analyze from the data set, at least temperature data and light radiation data in order to provide a set of temperature corrected light radiation data, wherein the device further includes synthesis circuitry configured to assess a user lifestyle from a set of information supplied by said analysis circuitry, and to provide recommendations for improvement of the user lifestyle, said recommendations including:

defining a minimum and/or maximum dose of exposure to a radiation having a wavelength smaller than 400 nm, a minimum and/or maximum dose of exposure to phototoxic blue light having a wavelength between 400 and 460 nm, and a minimum and/or maximum dose of exposure to non-visual blue light having a wavelength between 460 and 500 nm.

2. The device according to claim 1, wherein the storage circuitry is further configured to receive and store geographic coordinates data, the analysis circuitry being further configured to analyze a set of geographic coordinates data acquired all along the period of time in order to compute sunrise and sunset hours in view of providing the user information regarding times for exposure to daylight and/or going to bed.

3. The device according to claim 1, in which the measurement sensor includes a Global Positioning System (GPS) unit configured to acquire geographic coordinates data.

4. The device according to claim 1, further comprising a communication circuit configured to receive geographic coordinates data sent from an apparatus, said apparatus including a GPS configured to acquire and/or store said geographic coordinates data.

5. The device according to claim 1, in which said measurement sensor is further configured to be worn by the user in a second wearing position different from the first wearing position.

6. The device according to claim 5, wherein the first wearing position is on the wrist and the second wearing position is on an eyeglass frame.

7. The device according to claim 5, wherein, in the first wearing position, the temperature measurement sensor is further configured to measure the skin temperature and, in the second wearing position, the temperature measurement sensor is further configured to measure the environment temperature.

8. The device according to claim 7, wherein the analysis circuitry is configured to analyze, from the data set, at least one among temperature data, acceleration data, inclination data and light radiation data in order to compute user bedtime.

9. The device according to claim 8, wherein the analysis circuitry is configured to analyze, from said data set, at least one among temperature data and inclination data and acceleration data and light radiation data, in order to provide information on the user sleep/wake state.

10. The device according to claim 1, further comprising a wristband and/or temporary fixing device configured to affix the measurement circuit to an eyeglass frame, said wristband being configured to affix said measurement circuit to the wristband.

11. The device according to claim 1, further comprising a user interface configured to provide and/or acquire information to/from the user or to/from an expert.

12. The device according to claim 11, wherein said user interface includes at least one chosen among a display only or touchscreen, an audible signal circuit, a vibrating circuit and a push-button.

13. The device according to claim 1, wherein the at least one measurement circuit includes a plurality of measurement circuits, and further comprising a communication circuit configured to provide communication between at least two of the plurality of measurement circuits, the storage circuitry, the analysis circuitry, the synthesis circuitry, the user interface, and at least one of a home apparatus and a mobile phone.

14. The device according to claim 11, further comprising a communication circuit configured to provide communication between at least one of the measurement circuit, the storage circuitry, the analysis circuitry, the synthesis circuitry, the user interface, and at least one of a home apparatus and a mobile phone.

15. The device according to claim 1, wherein the light radiation measurement sensor includes at least one multi-spectral sensor configured to measure wavelengths ranging from 290 nm to 1150 nm over at least eight spectral bands, including at least one in the UV range and at least one in the infrared range.

16. The device according to claim 1, further comprising a casing, the measurement circuit and the analysis circuitry being installed in the casing.

17. The device according to claim 16, wherein the synthesis circuitry is installed in the casing.

18. The device according to claim 1, wherein the recommendations further include at least one of a group consisting of:

defining a minimum and/or maximum dose of exposure to daylight and/or artificial light, defining a minimum and/or maximum dose of exposure to photopic light having a wavelength of between 380 and 780 nm and/or to infrared light having a wavelength above 780 nm, defining one or more spectrum of artificial light suitable to the user at a given time of the day, controlling a least one home apparatus, in particular turning a light on or off, or dimming or brightening a light, or modifying the spectrum of a light, or opening or closing blinds, or modifying a room temperature, and defining a schedule for sleeping and/or awakening and/or exposing the user to daylight and/or said artificial light, and/or controlling said apparatus.

\* \* \* \* \*